(12) United States Patent
Hoffman et al.

(10) Patent No.: US 7,030,071 B2
(45) Date of Patent: Apr. 18, 2006

(54) SOLID-WATER DETOXIFYING REAGENTS FOR CHEMICAL AND BIOLOGICAL AGENTS

(75) Inventors: Dennis M. Hoffman, Livermore, CA (US); Ing Lap Chiu, Castro Valley, CA (US)

(73) Assignee: The Regents of the University of California, Oakland, CA (US)

( * ) Notice: Subject to any disclaimer, the term of this patent is extended or adjusted under 35 U.S.C. 154(b) by 593 days.

(21) Appl. No.: 10/085,512

(22) Filed: Feb. 26, 2002

(65) Prior Publication Data

US 2003/0160209 A1 Aug. 28, 2003

(51) Int. Cl.
- A62D 3/00 (2006.01)
- C01B 15/055 (2006.01)
- C01B 15/01 (2006.01)
- C01B 11/06 (2006.01)

(52) U.S. Cl. ............... 510/110; 510/367; 422/120; 424/406; 424/408; 588/299; 588/313; 588/320; 588/400; 588/401; 588/405; 588/408; 588/409; 252/186.28; 252/186.29; 252/186.36; 252/186.31

(58) Field of Classification Search .......... 588/299, 588/313, 320, 400, 401, 405, 408, 409; 252/186.28, 252/186.29, 186.3, 186.31, 183.36, 186.33, 252/194; 510/110, 367; 422/120; 424/406, 424/408; 516/15
See application file for complete search history.

(56) References Cited

U.S. PATENT DOCUMENTS

| | | | |
|---|---|---|---|
| 3,393,155 A | | 7/1968 | Schutte et al. |
| 3,810,842 A | * | 5/1974 | Steyermark ............ 510/110 |
| 4,008,170 A | | 2/1977 | Allan |
| 5,342,597 A | | 8/1994 | Tunison, III |
| 5,380,764 A | * | 1/1995 | Herzog ............... 514/725 |
| 5,445,756 A | | 8/1995 | Didier et al. |
| 5,938,288 A | | 8/1999 | Saint-Pierre et al. |
| 5,958,288 A | | 9/1999 | Mueller et al. |
| 5,972,196 A | * | 10/1999 | Murphy et al. ......... 205/466 |
| 5,998,691 A | * | 12/1999 | Abel et al. ............. 149/124 |
| 6,015,506 A | | 1/2000 | Streinz et al. |
| 6,139,763 A | | 10/2000 | Ina et al. |
| 6,245,957 B1 | * | 6/2001 | Wagner et al. .......... 588/316 |
| 6,387,241 B1 | * | 5/2002 | Murphy et al. .......... 205/626 |
| 6,455,751 B1 | * | 9/2002 | Hoffman et al. ........ 588/320 |
| 6,464,867 B1 | * | 10/2002 | Morita et al. .......... 210/202 |
| 6,569,353 B1 | * | 5/2003 | Giletto et al. ........ 252/186.28 |
| 6,570,048 B1 | * | 5/2003 | Getman et al. .......... 588/318 |
| 6,723,890 B1 | * | 4/2004 | Tucker et al. .......... 588/318 |
| 6,723,891 B1 | * | 4/2004 | Wagner et al. .......... 588/316 |

FOREIGN PATENT DOCUMENTS

| | | |
|---|---|---|
| JP | 08277204 A2 | 10/1995 |
| JP | 08-277204 | * 10/1996 |
| WO | WO 98/22554 A1 | 5/1998 |

OTHER PUBLICATIONS

JP Patent Office's English Language Machine Translation of JP Patent Publication No. 08-277204 (Oct. 22, 1996).*

* cited by examiner

Primary Examiner—Joseph D. Anthony
(74) Attorney, Agent, or Firm—John P. Wooldridge; L. E. Carnahan; Alan H. Thompson

(57) ABSTRACT

Formation of solid-water detoxifying reagents for chemical and biological agents. Solutions of detoxifying reagent for chemical and biological agents are coated using small quantities of hydrophobic nanoparticles by vigorous agitation or by aerosolization of the solution in the presence of the hydrophobic nanoparticles to form a solid powder. For example, when hydrophobic fumed silica particles are shaken in the presence of IN oxone solution in approximately a 95:5-weight ratio, a dry powder results. The hydrophobic silica forms a porous coating of insoluble fine particles around the solution. Since the chemical or biological agent tends to be hydrophobic on contact with the weakly encapsulated detoxifying solution, the porous coating breaks down and the detoxifying reagent is delivered directly to the chemical or biological agent for maximum concentration at the point of need. The solid-water (coated) detoxifying solutions can be blown into contaminated ventilation ducting or other difficult to reach sites for detoxification of pools of chemical or biological agent. Once the agent has been detoxified, it can be removed by flushing the area with air or other techniques.

5 Claims, No Drawings

SOLID-WATER DETOXIFYING REAGENTS FOR CHEMICAL AND BIOLOGICAL AGENTS

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to detoxifying chemical and biological agents, particularly, to providing detoxifying reagents for chemical and biological agents, and more particularly to the formation of coated solutions of detoxifying reagents using small quantities of treated (hydrophobic) nanoparticles, which results in a dry powder (solid-water), which can be deposited, such as by blowers, on difficult to reach sites for detoxification chemical or biological agents located at such sites.

Since the Saran incident in a Japanese subway, the possibility of terrorist attack with chemical or biological weapons has received increased attention. There has been developed sprayable solid-water detoxification reagents, which on contact with chemical agents will release the detoxifying reagent and attack the sulfur bond in mustard or in VX agents and the carbon bond in G agents, thereby detoxifying them. Preliminary experiments with chloroethyl ethyl sulfide as a mustard surrogate have shown that the encapsulated solid is released into the pool of surrogate and the "agent" was destroyed in 30 minutes. These types of oxidizer have also been shown to destroy the Anthrax stimulant *Bacillus globigii* (BG) and the VX surrogate, Amiton.

Currently, aqueous solutions or foams or other decontaminating agents have been used directly on the chemical or biological agent. Since the decontaminating chemicals are delivered everywhere, the chemical reactions associated with detoxification occur throughout the area of application, thereby providing the potential for causing collateral damage to the area surrounding the chemical or biological agents. Thus, there has been a need to provide decontaminating agents whereby depositing thereof at a point of need does not cause collateral damage to the area of application. Also, there is a need to provide remote areas such as ducting or other hard to reach areas with decontaminating chemicals without any cause of collaterial damage thereto.

The present invention provides a solution to the above-referenced problems associated with the deposition of decontaminating chemicals used on chemical or biological agents. In the invention, a liquid detoxifying reagent is weakly encapsulated with a hydrophobic nanoparticle coating to produce a powder or "solid-water detoxification reagent" which is "solid" until it contacts the spill of agent, and then the weak, nanoparticle coating breaks down, the detoxifying reagent solution is released and the chemical or biological agent is detoxified. This approach is based on the well-known phenomena called "Dry Water", see Degussa Corporation, Technical Bulletin Pigments No. 23 (1989), "Aerosil as a Thickening Agent for Liquid Systems", and Degussa Corporation Manuscript "Dry Water—a formulation principle with hydrophobic Aerosil®".

SUMMARY OF THE INVENTION

It is an object of the present invention to provide decontaminating agents for use on chemical or biological agents.

A further object of the invention is to provide solid-water detoxification reagents for chemical and biological agents.

A further object of the invention is to provide solid-water detoxification reagents wherein only contaminated areas see the reactive ingredients, reducing collateral damage to surrounding areas.

Another object of the invention is to encapsulate solutions of detoxifying reagents using small quantities of treated (hydrophobic) nanoparticles.

Another object of the invention is to coat detoxifying reagents with hydrophobic nanoparticles by vigorous agitation or by aerosolization of the reagents in the presence of hydrophobic nanoparticles to form a solid powder.

Another object of the invention is to produce solid-water detoxifying reagents for chemical and biological agents which for example have a 95:5-weight ratio of the detoxifying reagent to the encapsulating hydrophobic nanoparticles.

Another object of the invention is to provide solid-water detoxifying reagents which can be deposited at a point of use, such as by air blowers, for detoxification of pools of chemical or biological agents without collateral damage to surrounding non-contaminated areas.

Another object of the invention is to provide solid-water detoxifying reagents that can be deposited in hard-to-reach areas containing chemical or biological agents and which cause no collateral damage to non-contaminated areas.

Other objects and advantages of the present invention will become apparent to those skilled in the art in view of the following description. The invention involves solid-water detoxifying reagents for chemical and biological agents. In accordance with the invention, solutions of detoxifying reagent for chemical and biological agents are coated using small quantities of treated (hydrophobic) nanoparticles by either vigorous agitation or by aerosolization of the solution in the presence of hydrophobic nanoparticles to form a solid powder. For example, when hydrophobic fumed silica particles (see Cabot Corporation Technical Date TSD-131(October 1998), "Cab-O-Sil TS-530 Treated Fumed Silica") are shaken in the presence of 1N oxone solution in approximately a 95:5-weight ratio, a dry powder results. Also, a weight ratio of 80:20 has been utilized. The hydrophobic silica forms a porous coating of insoluble fine particles around the solution. Since the chemical or biological agent tends to be hydrophobic, on contact with the weakly encapsulated detoxifying, the porous coating breaks down and the detoxifying reagent is delivered directly to the chemical or biological agent for maximum concentration at the point of need. Solutions of detoxifying reagents should be encapsulated by 5% of an appropriately treated colloidal solid, such as hydrophobic fumed silica. The "solid-water" detoxifying solutions can be blown into contaminated ventilation ducting or other difficult to reach sites for detoxification of pools of chemical or biological agents. Low-pressure air sprayers, blowers, or other techniques can apply the encapsulated detoxifying reagent. Only the contaminated area where the encapsulation breaks down see the reactive ingredients (detoxifying reagent), reducing collateral damage to duck work or other sensitive equipment. The rest of the thus delivered "solid-water" detoxifying reagent can be removed at a low point in the ducting or vacuumed out. Once the agent has been detoxified, it can be removed by flushing the area with air or other techniques.

DETAILED DESCRIPTION OF THE INVENTION

The present invention involves solid-water detoxifying reagents for chemical and biological agents. A liquid detoxifying reagent is weakly encapsulated with, for example, a 3–7% hydrophobic nanoparticle coating to produce a powder of typically 95% by weight detoxifying solution. This "solid-water detoxification reagent" is "solid" until it contacts the spill of a chemical or biological agent, then the weak, nanoparticle coating breaks down, the detoxifying reagent solution is released and the chemical or biological agent is detoxified. This approach is based on the well-known phenomena called "Dry Water", referenced above. Because the active ingredients of the reagent solution are released on contact with the agent to be detoxified, they do not cause collateral damage to ducting or other areas where the solid-water detoxifying reagent has not lost its protective coating. Residual solid-water detoxifying reagent can be collected at a low point in the structure or vacuumed out. Once the chemical or biological agent has been detoxified, it can be removed by flushing the area with air or by other techniques.

Solutions of detoxifying reagent can be coated using small quantities of treated (hydrophobic) nanoparticles by vigorous agitation, or by aerosolization of the solution in the presence of the hydrophobic nanoparticle to form a solid powder. For example, when hydrohobic fumed silica particles are shaken in the presence of 1N oxone solution in approximately a 95:5-weight ratio of solution to particles, a dry powder results. Solutions of detoxifying reagents, such as hydrogen peroxide, potassium permanganate, sodium hypochloride, ammonium persulfate, or ammonium peroxymono sulfate, should be readily encapsulated by 5% of the appropriately treated colloidal solids, such as hydrophobic fumed silica, alumina, clays and other refractory oxides treated with a hydrophobic chemical.

In carrying out the present invention, a solution of detoxifying reagent is prepared or purchased from a commercial supplier at the appropriate strength and composition to decontaminate a selected chemical or biological agent. Several methods of droplet formation are possible for coating the surface of the detoxifying reagent solution with small quantities (4–7%) of hydrophobic nanoparticle. The hydrophobic nanoparticle can be added to the solution followed by agitation of the solution, or the solution can be sprayed or dripped into the hydrophobic nanoparticle with agitation. Water was successfully encapsulated with three commercial hydrophobic silicas and one developmental product with about 5% hydrophilic silica.

During experimental verification of the invention, 25 gram quantities of 1N oxone solution was encapsulated with Cab-o-Sil TS 530 treated fumed silica, made by Cabot Corporation, to make solid powder at 95/5 wt/wt ratio and called "dry oxone". The "dry oxone" was tested against CEES (mustard surrogate). The CEES was completely absorbed by the "dry oxone" and no residual CEES was found after 30 minutes.

Alternate colloidal nanoparticles, such as alumina or clays, could be treated with a hydrophobic chemical to alter their surface characteristics and used to encapsulate detoxifying solutions.

Aqueous or mixed solvent solutions of detoxifying reagents, such as hydrogen peroxide, potassium permanganate, sodium hypochlorite, ammonium persulfate, ammonium peroxymonosulfate, or others can be readily encapsulated with as low as 3–4%, but more typically, 5–7% hydrophobic colloidal solids. High concentrations of hydrogen peroxide tended to decompose, generating oxygen, which means that encapsulated hydrogen peroxide would best be prepared just prior to use. The other reagent solutions appear to be quite stable. The encapsulated reagent solutions tend to loose solvent slowly by evaporation overtime, but can be kept in sealed containers for some period of time, possibly months to years.

"Dry water" mock of detoxifying reagent can be sprayed into ducting, for example, using low-pressure air or other conventional solid transport equipment, as discussed above. However, this powder will also collapse when it comes in contact with certain organic liquids with an affinity for water. Thus, the detoxifying of chemical and biological agents using the solid-water detoxifying reagents of this invention would be less affective in high moisture areas than in low moisture areas.

As pointed out above, cleanup can be as simple as vacuuming out the solid particles for reuse. Once the chemical or biological agent has been detoxified, it can be volatilized away with air or adsorbed on various absorbents and removed.

The solid-water detoxifying reagents of this invention can be used for detoxification of chemical or biological agents from a terrorist attack, accidental release, or military applications. These reagents are specifically designed to decontaminate ducting, and inaccessible areas of buildings where the chemical or biological agents have been applied and cannot be easily reached by decontamination personnel. These reagents can be used for recovery of contaminated equipment. Simple kits can be prepared for emergency use as required. Large scale detoxification is possible with appropriate equipment. Because of the release of the active reagent only on contact with the desired chemical or biological agent, minimal collateral damage would occur.

It has thus been shown that the present invention provides for decontamination of chemical or biological agents which can be delivered to a desired point of use without causing collateral damage to the surrounding area or associated equipment. The detoxifying reagent is encapsulated in a material that will release the active reagent, thereof upon contact with a chemical or biological agent, and the solid-water detoxifying reagent can be formulated to an appropriate strength to decontaminate a specific chemical or biological agent. Thus, the present invention provides a significant advance in the field of detoxification of various materials which can be utilized as undesirable chemical or biological agents.

While particular examples, materials, parameters, etc. have been described to exemplify and teach the principles of the invention, such is not intended to be limiting. Modifications and changes may become apparent to those skilled in the art, and it is intended that the invention be limited only by the scope of the appended claims.

What is claimed is:

1. A solid-water material for detoxifying a hydrophobic chemical agent or a hydrophobic biological agent, comprising:
   a detoxifying reagent, and
   a hydrophobic nanoparticle material encapsulating said detoxifying reagent to form a porous coating, wherein said hydrophobic nanoparticle material comprises a weight that is 3–7% of the weight of said detoxifying reagent, wherein when said hydrophobic nanoparticle material contacts said hydrophobic chemical agent or said hydrophobic biological agent, said porous coating breaks down and said detoxifying reagent is delivered directly to said hydrophobic chemical agent or said hydrophobic biological agent.

2. The solid-water material of claim 1, wherein said detoxifying reagent is composed of an aqueous or mixed solvent solution containing at least one active reagent.

3. The solid-water material of claim 1, wherein said detoxifying reagent is selected from the group consisting of hydrogen peroxide, potassium permanganate, sodium hypochlorite, ammonium persulfate, ammonium peroxymonosulfate, and an oxidizing agent.

4. The solid-water material of claim 1, wherein said hydrophobic material is selected from the group consisting of silica, alumina, clay, and other refractory oxides.

5. The solid-water material of claim 1, wherein said detoxifying reagent is composed of 1N oxone solution, and wherein said hydrophobic material is composed of treated fumed silica.

* * * * *